(12) United States Patent
Pratt

(10) Patent No.: US 6,989,092 B1
(45) Date of Patent: Jan. 24, 2006

(54) BAILER HAVING BUILT-IN FILTER

(76) Inventor: David W. Pratt, 13512 Feather Sound Cir., Clearwater, FL (US) 33762

( * ) Notice: Subject to any disclaimer, the term of this patent is extended or adjusted under 35 U.S.C. 154(b) by 328 days.

(21) Appl. No.: 10/250,216

(22) Filed: Jun. 13, 2003

(51) Int. Cl.
*B01D 35/02* (2006.01)

(52) U.S. Cl. ............... 210/136; 210/448; 210/452; 73/864.63; 294/68.22

(58) Field of Classification Search .. 294/68.22–68.26; 73/864.63, 864.65; 166/168, 167, 162; 210/136, 210/448, 452, 454, 464, 453, 445, 463
See application file for complete search history.

(56) References Cited

U.S. PATENT DOCUMENTS

| | | | | |
|---|---|---|---|---|
| 1,292,737 A | * | 1/1919 | Endreson | ............ 210/117 |
| 1,557,823 A | * | 10/1925 | Frattallone | ............ 294/68.22 |
| 6,464,012 B1 | * | 10/2002 | Strickland | ............ 166/369 |

* cited by examiner

Primary Examiner—Terry K. Cecil
(74) Attorney, Agent, or Firm—Ronald E. Smith; Smith & Hopen, P.A.

(57) ABSTRACT

In a first embodiment, a top-emptying bailer has a cylindrical filter positioned within a hollow interior of the bailer. A bottom, leading end of the filter is capped by an imperforate bottom fitting having an insert that fits into the hollow interior of the filter. The top, trailing end of the filter receives a cylindrical insert that together with the imperforate bottom fitting insert helps hold the filter open as liquid fluid flows into it. The filter is preferably formed of polypropylene. The bailer is inverted so that liquid fluid in the hollow interior of the bailer is constrained to flow through the filter before it exits the trailing end of the bailer. In a second embodiment, the filter is positioned at the leading end of the bailer and the bailer is emptied from the bottom.

15 Claims, 6 Drawing Sheets

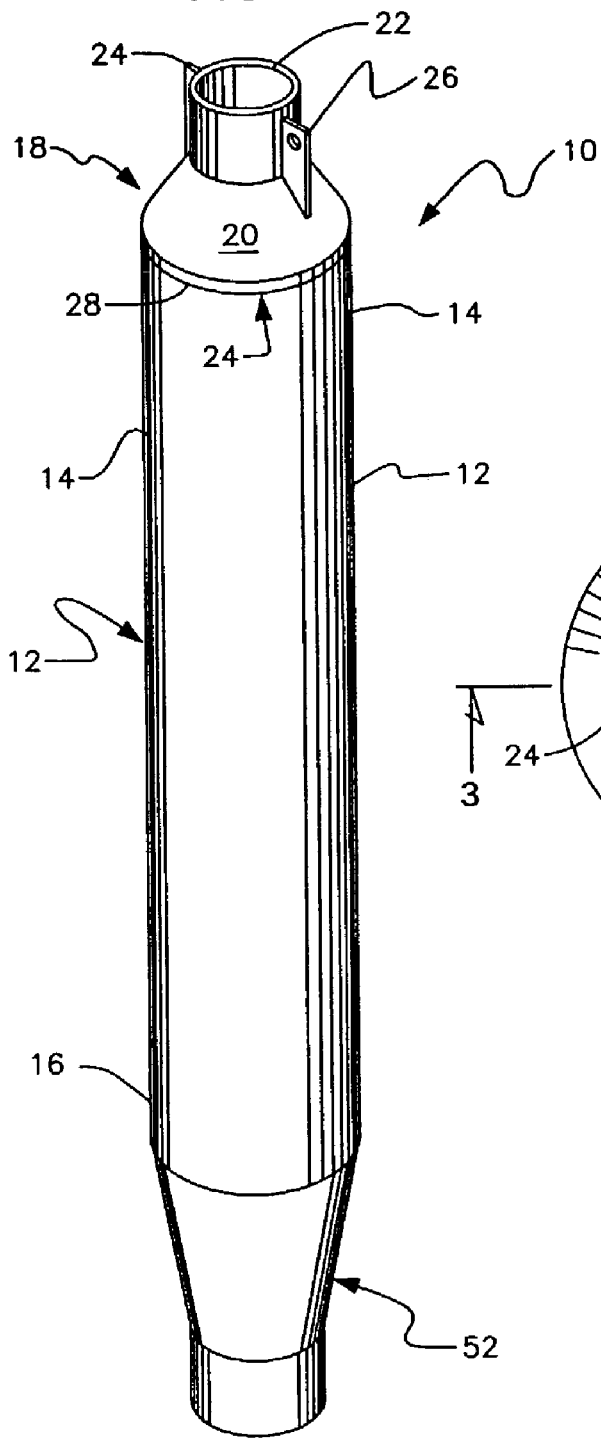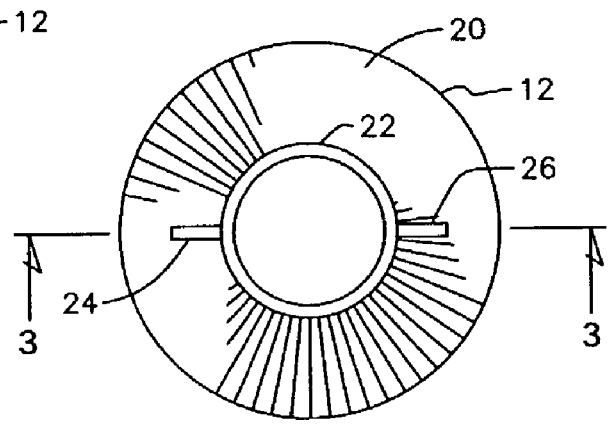

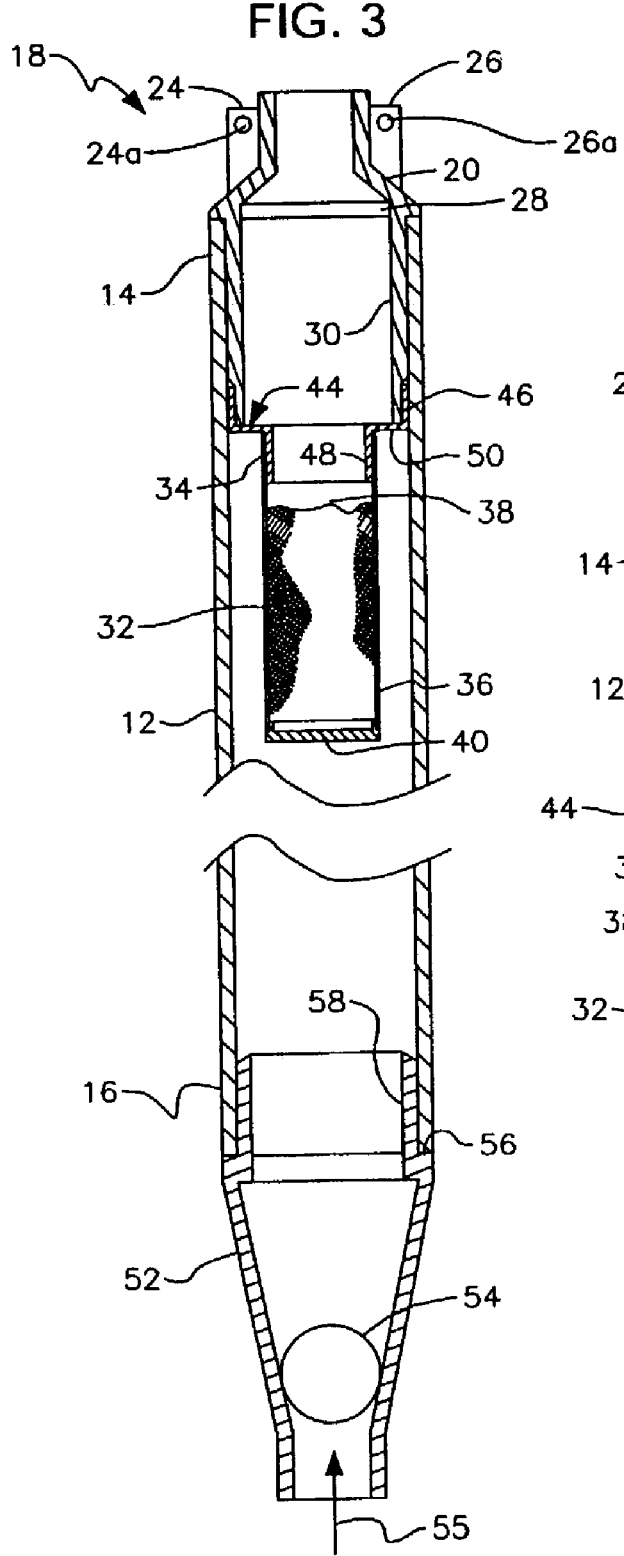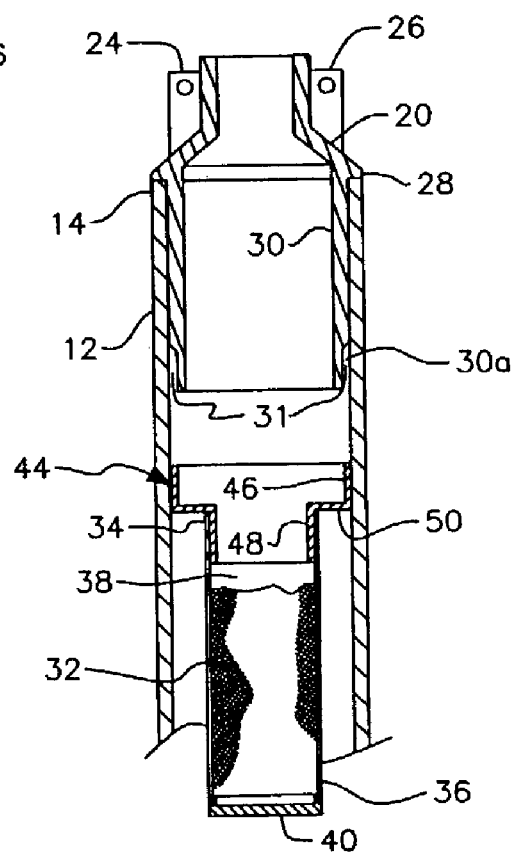
FIG. 3
FIG. 4

FIG. 7A
FIG. 7B
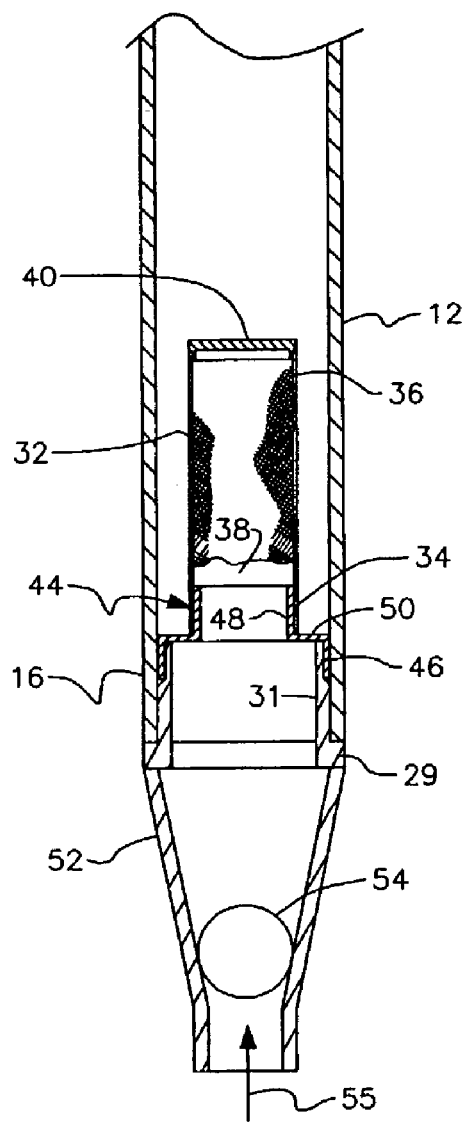
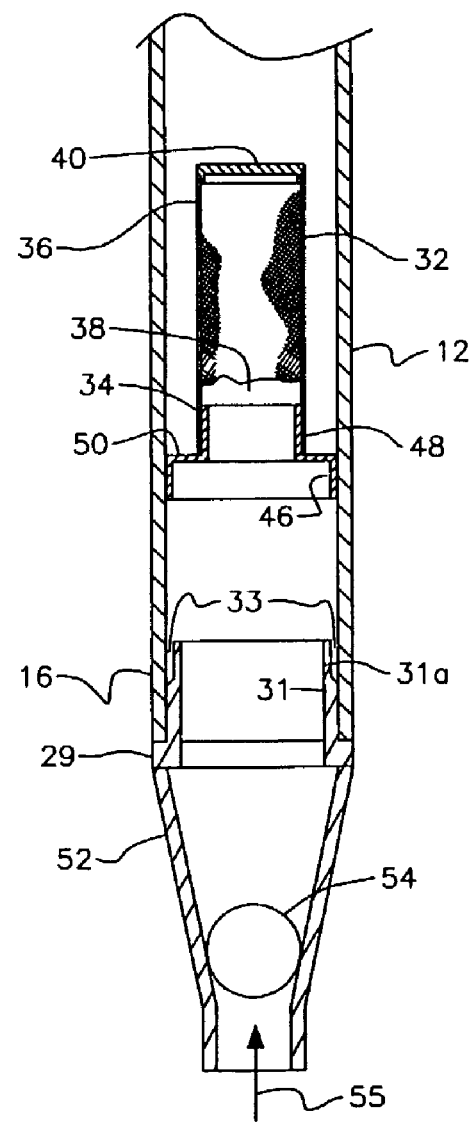

BAILER HAVING BUILT-IN FILTER

BACKGROUND OF INVENTION

1. Field of the Invention

This invention relates, generally, to bailers. More particularly, it relates to a bailer having a built-in filter.

2. Description of the Prior Art

It is customary practice to filter liquid fluid collected by a bailer to remove therefrom sediment or other particles that are not needed by a laboratory performing an analysis of the sample. The same personnel who collect the sample perform the filtering process in the field.

Typically, the bailer is held upright and emptied from the bottom by using a device, commonly known as a VOC device, to open a check valve so that the liquid fluid drains from the bailer, through the VOC device, through a filter positioned in fluid communication with the downspout of the VOC device, through a hose connected to the filter, and into a container positioned below the filter to collect the filtered sample for subsequent analysis in a remote laboratory.

The filter includes filter material packed within a housing. There are a large variety of filter housings in commercial use, each designed for specific uses. Thus, when a bailer is purchased for use in an area where sediment or other particles are present to the extent that filtering is required prior to laboratory analysis, then an appropriate filter must also be purchased. Since a filter may retain residual amounts of the filtered material, each filter is typically used just one time.

Another drawback of filters as they are now known is that they present mechanical difficulties in their handling. As mentioned above, the bailer must be held upright, the VOC device must be placed into the bottom of the bailer at the bailer downspout to lift a check ball or other valve means from its seat, and the filter must be positioned in fluid communication with the outlet of the VOC device before liquid fluid begins flowing therethrough. At the same time, a container for collecting the filtered liquid fluid must be positioned in fluid communication with the hose that extends from the filter.

Since the known filters are relatively expensive to purchase and transport, bulky to handle and not easy to use, the user of a bailer may collect a sample having excessive particulate matter and deliver such unsatisfactory sample to the lab for analysis without taking the time to filter the sample as needed.

It is also important to appreciate that two (2) people are required to handle the filtering job. One person holds the bailer in one hand and holds the VOC device in the other. This enables a second person to hold the filter in one hand and the container in the other.

What is needed, then, is an improvement to bailers that makes the filtering task easier.

It would also be very advantageous if a bailer construction could be invented that would enable a single individual to perform the filtering operation. Such an improvement would double productivity by cutting in half the number of people required to collect and filter samples in the field.

However, in view of the prior art considered as a whole at the time the present invention was made, it was not obvious to those of ordinary skill in the pertinent art how the art of bailers and filters could be advanced.

SUMMARY OF INVENTION

The long-standing but heretofore unfulfilled need for an improved means for filtering liquid fluid collected by a bailer is now met by a new, useful, and nonobvious invention. The novel bailer includes a built-in filter so that there is no need to purchase a separate filter. Moreover, because the filter is built-in, the difficulty of handling a filter, a VOC device, a sample collection container, and a bailer all at the same time is eliminated. Thus, a single person can handle the sample collection and filtration procedures.

The novel bailer construction includes a main body having an elongate, cylindrical configuration and a hollow interior. The main body has a trailing end and a leading end.

A top member is mounted to the trailing end of the main body and a check valve housing is mounted to the leading end of the main body.

A check valve means is disposed within the check valve housing and is adapted to admit liquid flow into the hollow interior of the main body when the leading end of the bailer enters into a body of liquid fluid and to close the leading end when liquid fluid has ceased to flow into the hollow interior.

The leading end of a bailer is the end that first enters the water or other liquid being sampled. In this particular invention, the trailing end of the bailer remains above the water level at all times, i.e., the bailer is not completely submerged.

In a first embodiment, a filter member of cylindrical structure has a trailing end, a leading end, and a hollow interior. The filter member is disposed within the hollow interior of the main body of the bailer. An imperforate cap or bottom fitting is secured to the leading end of the filter member so that water flowing into the hollow interior of the main body of the bailer cannot enter into the leading end of the filter.

The trailing end of the filter member is positioned near the open trailing end of the bailer and is in fluid communication with said open trailing end so that liquid fluid in the hollow interior of the filter may be poured out from said trailing end by inverting the bailer.

In a second embodiment, the leading end of the filter member is positioned near the leading end of the bailer and is in fluid communication with said leading end so that liquid fluid in the hollow interior of the filter may be drained from said leading end without inverting the bailer.

In both embodiments, liquid fluid within the hollow interior of the bailer is constrained to flow through the filter member when the bailer is emptied. A need for an external filter member is thereby obviated, together with the need for a second person to hold an external filter during the bailer-emptying procedure.

The top member secured to the trailing end of the bailer (in both embodiments) includes an annular base, a depending wall of cylindrical structure that depends from said annular base and that is snugly and slidingly received within the trailing end of the main body of the bailer, and a mounting member that surmounts the annular base.

The mounting member that surmounts the annular base is adapted to be engaged by a pair of ropes that is used to lower the bailer into a body of liquid fluid and to raise the bailer from said body of liquid fluid.

More particularly, the mounting member includes a hollow frusto-conical part and a tubular part. The frusto-conical part performs a diameter-reducing function so that the diameter of the tubular part is less than the diameter of the main body of the bailer. A pair of flanges extend radially-outwardly from the tubular part in diametrically-opposed relation to one another. Each flange is apertured to receive a rope or other means for lowering and lifting the bailer into and out of, respectively, a body of liquid fluid.

The annular base of the top member has a diameter equal to the diameter of the bailer main body. Thus, the diameter of the annular base is slightly greater than the interior diameter of the main body and cannot enter thereinto. Accordingly, the leading end of the annular base lies flush against the trailing end of the main body of the bailer.

The outer diameter of the depending wall is substantially equal to the interior diameter of the main body, being just slightly smaller in diameter, so that said depending cylindrical wall is snugly and slideably received within the trailing end of the main body. The difference between the outer diameter of the annular wall and the outer diameter of the depending cylindrical wall is substantially equal to the thickness of the cylindrical wall that forms the main body of the bailer.

A diameter-reducing step is formed in the depending wall. The step is near the leading end of the depending wall and is provided in part to facilitate assembly of the novel bailer. An annular space is thereby created between the interior wall of the main body of the bailer and the outer wall of the reduced-diameter part of the depending wall. As will become clear as this disclosure proceeds, that annular space is occupied, at least in part, by an annular wall that forms the trailing end of a top fitting for the filter member.

A leading end of the filter member is secured to an imperforate bottom fitting that includes a disc-shaped base and a bottom insert formed integrally with said disc-shaped base and which is concentrically disposed with respect thereto. The insert extends into the hollow interior of the filter member. The difference in diameter between the disc-shaped base and the insert creates a radially-outwardly extending flange against which a leading end of the filter member abuts when the insert is fully inserted into the hollow interior of the filter member.

The trailing end of the filter member is engaged to a top fitting that has two parts. The first part has a cylindrical structure and an outer diameter substantially equal to the inner diameter of the main body of the bailer. The first part is snugly received within the hollow interior of said main body and in the first embodiment of the invention said first part is positioned near the trailing end of said main body.

The trailing end of the first part is snugly received within the annular space formed by the diameter-reducing step formed in the leading end of the wall that depends from the annular base of the top member.

The second part of the top fitting is also of cylindrical construction. The outer diameter of the second part is substantially equal to the internal diameter of the filter member so that said second part is snugly received within the hollow interior of the filter member.

An annular step is formed between the first part of the top fitting and the second part thereof because the diameter of the first part is greater than the diameter of the second part. The trailing end of the filter abuts against said annular step.

The outer diameter of the filter member is substantially less than the inner diameter of the hollow interior of the main body of the bailer. This allows liquid fluid within the bailer to flow freely into the filter along its length.

The top fitting and the bottom fitting cooperate with one another to hold open the hollow interior of the filter member when liquid fluid flows thereinto.

In the second embodiment, the filter member is disposed at the leading end of the bailer in fluid communication with the check valve housing.

The primary object of this invention is to provide a bailer having a built-in filter so that a filter need not be purchased separately from a bailer.

A closely related object is to provide a bailer having a built-in filter to facilitate the filtering process by reducing the number of components that must be handled simultaneously to perform the filtering process.

Another important object is to reduce the number of individuals required to perform a filtering operation in the field.

Still another important object is to provide a bailer having a top-emptying embodiment where an internal filter is disposed near the trailing end of the bailer and a bottom-emptying embodiment where as internal filter is disposed near a leading end of the bailer.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 1 is a perspective view of the novel bailer;

FIG. 2 is a top plan view thereof;

FIG. 3 is a longitudinal sectional view taken along line 3—3 in FIG. 2;

FIG. 4 is a view like FIG. 3 but with the filter assembly separated from the top closure member;

FIG. 7A is a longitudinal sectional view of the second embodiment;

FIG. 7B is a view like FIG. 7A but with the filter assembly separated from the bottom closure member.

DETAILED DESCRIPTION

Figure 5:
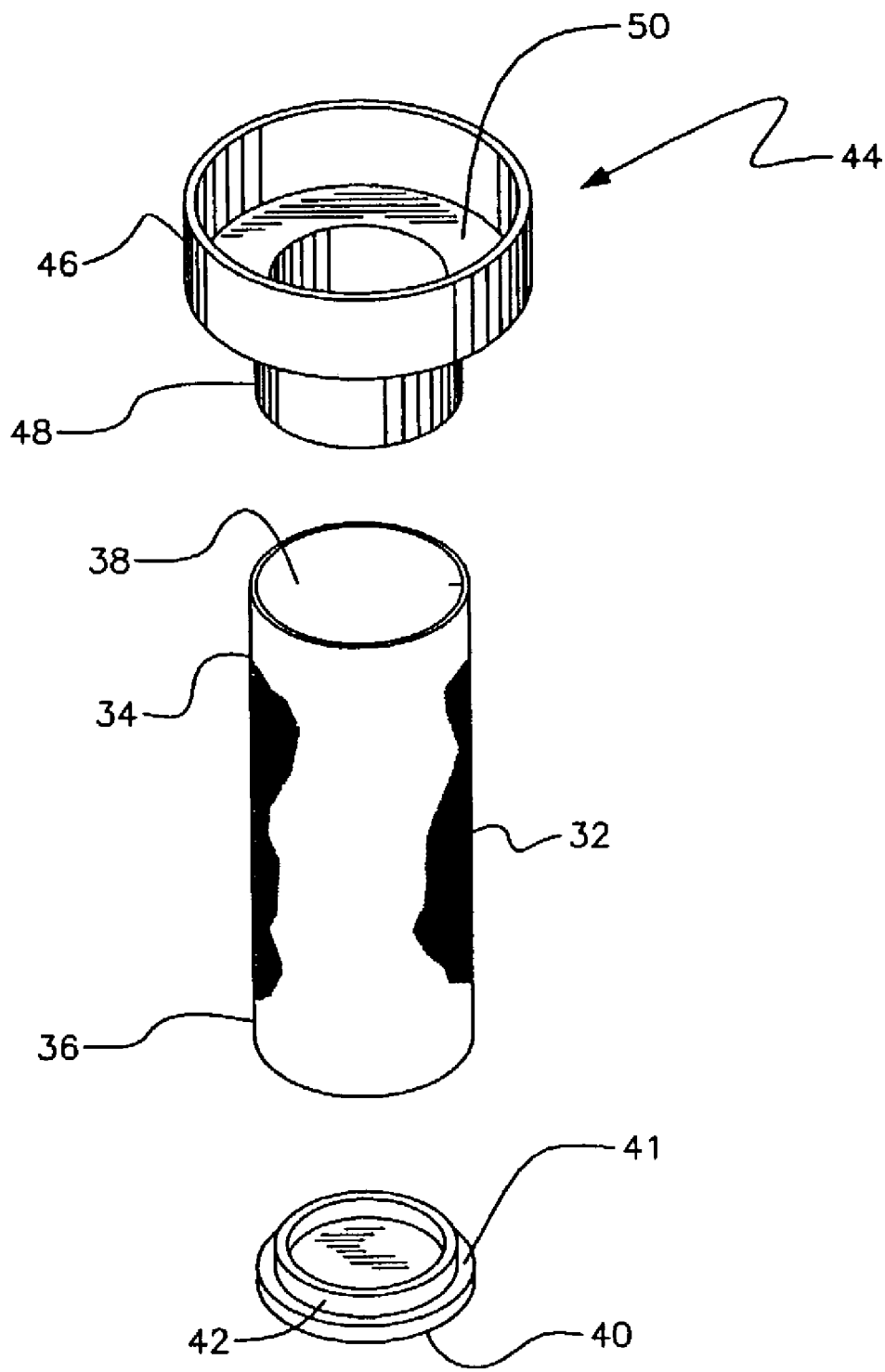
FIG. 5 is an exploded perspective view of a filter assembly.

Referring to FIGS. 1 and 2, it will there be seen that the reference numeral 10 denotes an illustrative embodiment of the present invention as a whole.

The leading end of a bailer is the end that first enters the water or other liquid being sampled. In this particular invention, the trailing end of the bailer remains above the liquid surface at all times, ie., bailer 10 is not completely submerged.

The novel bailer construction includes a main body 12 having an elongate, cylindrical configuration and a hollow interior. The main body has a trailing end 14 and a leading end 16.

Prior to insertion of bailer 10 into the liquid fluid, main body 12 is positioned in a vertical plane in normal relation to the surface of the body of liquid fluid with leading end 16 nearest said surface.

Top member 18 is mounted to trailing end 14 of main body 12. As best understood in connection with FIG. 3, top member 18 includes hollow frusto-conical part 20, tubular part 22, and flanges 24, 26 that are integrally formed with and extend radially outwardly from tubular part 22 in diametrically opposing relation to one another. Each flange is apertured as at 24a, 26a (FIG. 3). Apertures 24a, 26a are adapted to be engaged by a pair of ropes, not illustrated, that is used to lower bailer 10 into a body of liquid fluid and to raise bailer 10 from said body of liquid fluid.

Frusto-conical part 20 performs a diameter-reducing function so that tubular part 22 has less diameter than main body 12.

Top member 18 is secured to trailing end 14 of main body 12 of bailer 10 in both embodiments. As depicted in FIGS. 3 and 4, top member 18 further includes annular base 28. Wall 30 of cylindrical structure depends from annular base 28 and is snugly and slidingly received within trailing end 14 of main body 12.

Annular base 28 has an outer diameter substantially equal to the outer diameter of bailer main body 12. Thus, the outer diameter of annular base 28 is slightly greater than the inner diameter of main body 12 and cannot enter thereinto.

Depending wall 30 depends from annular base 28 as aforesaid and has an outer diameter substantially equal to the inner diameter of main body 12. Thus, depending wall 30 is snugly and slideably received within trailing end 14 of main body 12. One or more spot welds, or other suitable attachment means, may be employed to prevent separation of said depending wall 30 from said main body.

As depicted in FIGS. 3 and 4, the difference between the outer diameter of annular base 28 and the outer diameter of depending wall 30 is substantially equal to the thickness of the cylindrical wall that forms main body 12 of bailer 10. Accordingly, the leading surface of annular base 28 lies flush against the trailing end of main body 12 of bailer 10 and limits the depth of insertion of cylindrical wall 30 into the hollow interior of main body 12.

A diameter-reducing step 30a is formed in the leading end of depending wall 30. Step 30a is provided in part to facilitate assembly of the novel bailer. Annular space 31 (FIG. 4) is thereby created between the interior surface of main body 12 of bailer 10 and the outer surface of the reduced-diameter part of depending wall 30. As will become clear as this disclosure proceeds, annular space 31 is occupied, at least in part, in the first embodiment of this invention, by an annular wall that forms the trailing end of a top fitting for the filter member disclosed hereinafter.

Filter member 32 of cylindrical structure has a trailing end 34, a leading end 36, and a hollow interior 38. Filter member 32 is disposed within the hollow interior of main body 12 of bailer 10 and said filter member is preferably formed of polypropylene. Filter members formed of different materials are also within the scope of this invention.

Filter member 32 is preferably of cylindrical construction although it could have a cross-section of any other configuration such as an irregular cross-section, elliptical, triangular, square, pentagonal, and the like.

Filter member 32 is installed within the hollow interior of main body 12 at the time bailer 10 is manufactured. The bailer user may select from a wide variety of filtration sizes when purchasing a bailer. Some filters may do little more than filter out particles of sand and other filters may filter out particles having diameters measured in angstroms.

An imperforate filter bottom fitting includes a disc-shaped base 40 and is secured to leading end 36 of filter member 32 to prevent liquid fluid flow into the hollow interior of filter member 32 at said leading end. As best depicted in FIG. 5, the bottom fitting further includes insert 42 that extends into the hollow interior of filter member 32. Insert 42 is integrally formed with disc-shaped base 40 and is positioned in concentric relationship thereto. The difference in diameter between base 40 and insert 42 creates an annular flange 41 having a radial extent that is substantially equal to the thickness of filter member 32. Accordingly, leading end 36 of filter member 32 abuts flange 41 when bottom insert 42 is fully inserted into hollow interior 38 of filter member 32.

Trailing end 34 of filter member 32 is engaged to a top fitting 44 (FIGS. 3–5) that has two parts. First part 46 has a cylindrical structure and an outer diameter substantially equal to the inner diameter of main body 12 of bailer 10. First part 46 is snugly received within the hollow interior of main body 12 and in the first embodiment of the invention said first part is positioned near trailing end 14 of main body 12.

More particularly, first part 46 is snugly received within annular space 31 formed by diameter-reducing step 30a formed in the leading end of depending wall 30. One or more spot welds, or other suitable attachment means, may be employed to prevent separation of first part 46 from depending wall 30.

Second part 48 of top fitting 44 is also of cylindrical construction. The outer diameter of second part 48 is substantially equal to the internal diameter of filter member 32 so that second part 48 is snugly received within hollow interior 38 of filter member 32.

Annular step 50 is formed between first part 46 of the top fitting and second part 48 thereof because the diameter of first part 46 is greater than the diameter of second part 48. Trailing end 34 of filter 32 abuts against said annular step 50 and said annular step 50 thus limits the depth of insertion of second part 48 into hollow interior 38 of filter 32.

Top fitting 44 and bottom fitting 40 cooperate with one another to hold open filter member 32 when liquid fluid flows thereinto.

A bottom closure member or check valve housing 52 is mounted to leading end 16 of main body 12.

As depicted in FIG. 3, a check valve means, here in the form of a check ball 54, is disposed within check valve housing 52 and is adapted to admit liquid flow into the hollow interior of main body 12 when leading end 16 of bailer 10 enters into a body of liquid fluid and to close leading end 16 when liquid fluid has ceased to flow into the hollow interior. Flow into said main body is indicated by directional arrow 55.

A diameter-reducing step 56 is formed in check valve housing 52 to create reduced diameter cylindrical part 58. The outer diameter of cylindrical part 58 is substantially equal to the inner diameter of main body 12 so that cylindrical part 58 is snugly and slideably received within the hollow interior of main body 12. The difference in diameter between the main part of check valve housing 52 and cylindrical part 58 is substantially equal to the thickness of main body 12. Diameter-reducing step 56 thus serves to limit the depth of insertion of cylindrical wall 58 into main body 12. One or more spot welds, or other suitable attachment means, may be employed to prevent separation of said cylindrical wall 58 from said main body.

In the first embodiment, depicted in FIGS. 3 and 4, trailing end 34 of filter member 32 is in open fluid communication with tubular part 22 of hollow top member 18 so that liquid fluid in hollow interior 38 of filter 32 may be poured out from said tubular part when bailer 10 is inverted.

Figure 6:
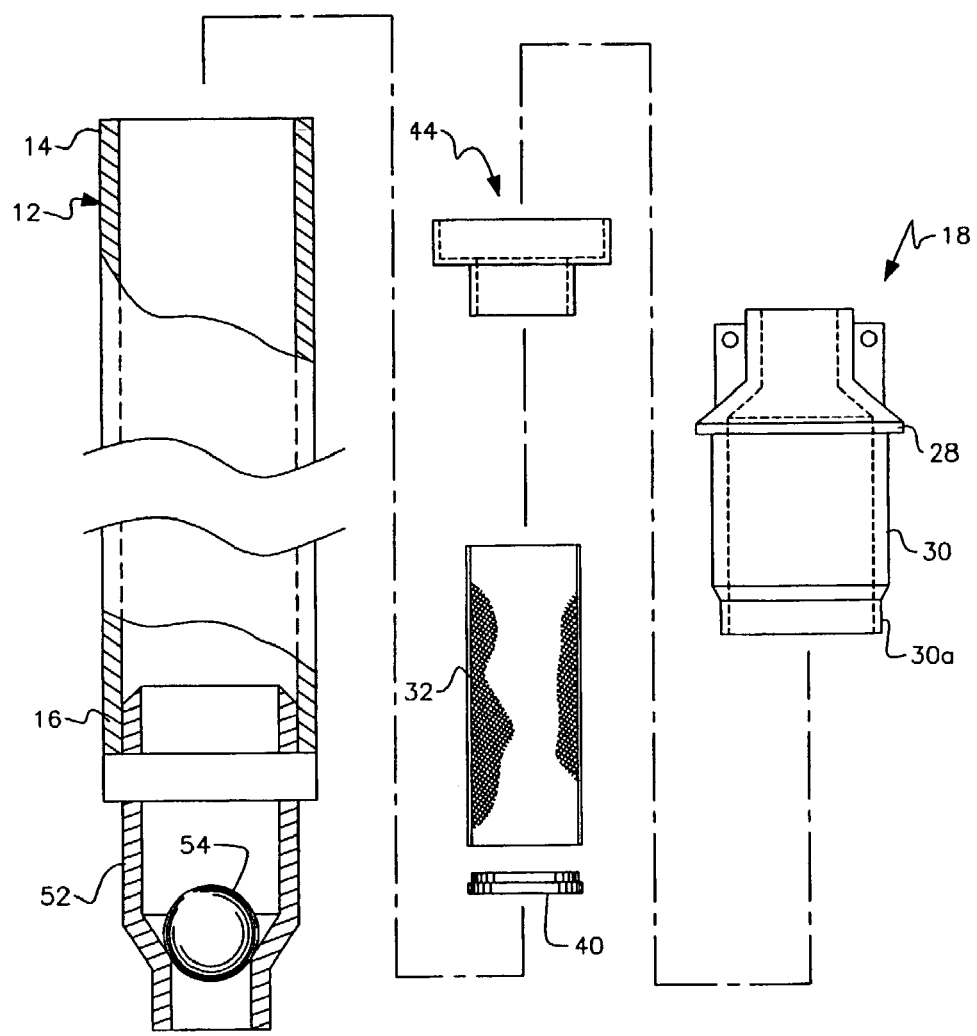
FIG. 6 is a side elevational, partially sectional assembly diagram depicting how the various parts of the first embodiment are connected to their contiguous parts.

FIG. 6 depicts how the above-described parts are assembled to form the first embodiment.

In a second embodiment, depicted in FIGS. 7A and 7B, end 34 of filter member 32 is positioned near leading end 16 of bailer 10 and is in valved fluid communication with said leading end so that liquid fluid in the hollow interior of filter 10 may be emptied from said leading end without inverting the bailer as in the first embodiment.

In this second embodiment, base 40 of the filter bottom fitting of the first embodiment is still labeled 40 because it is the same part as in the first embodiment but in this second embodiment the bottom fitting is a top fitting and is inverted from its first embodiment orientation. Top filter fitting 44 of the first embodiment is still labeled 44 because it is the same part as in the first embodiment but in this second embodiment it is a bottom fitting and is inverted from its first embodiment orientation.

As best understood by comparing FIGS. 7A and 7B, first part 46 of filter fitting 44 is snugly received within the hollow interior of main body 12 and is positioned in an annular space 33 defined by a diameter-reducing step 31a formed in wall 31 that projects upwardly from annular base 29. Annular base 29 and wall 31 collectively form a bottom member to which the filter assembly is secured when the filter is positioned near the leading end of the bailer. Wall 31 is positioned in concentric relation to annular base 29 and said wall has a diameter slightly less than the diameter of annular base 29. The difference in diameter is substantially equal to the thickness of the sidewalls of main body 12. Accordingly, annular base 29 abuts the leading edge of main body 12 and limits the depth of insertion of wall 31 into the hollow interior of said main body.

Figure 8:
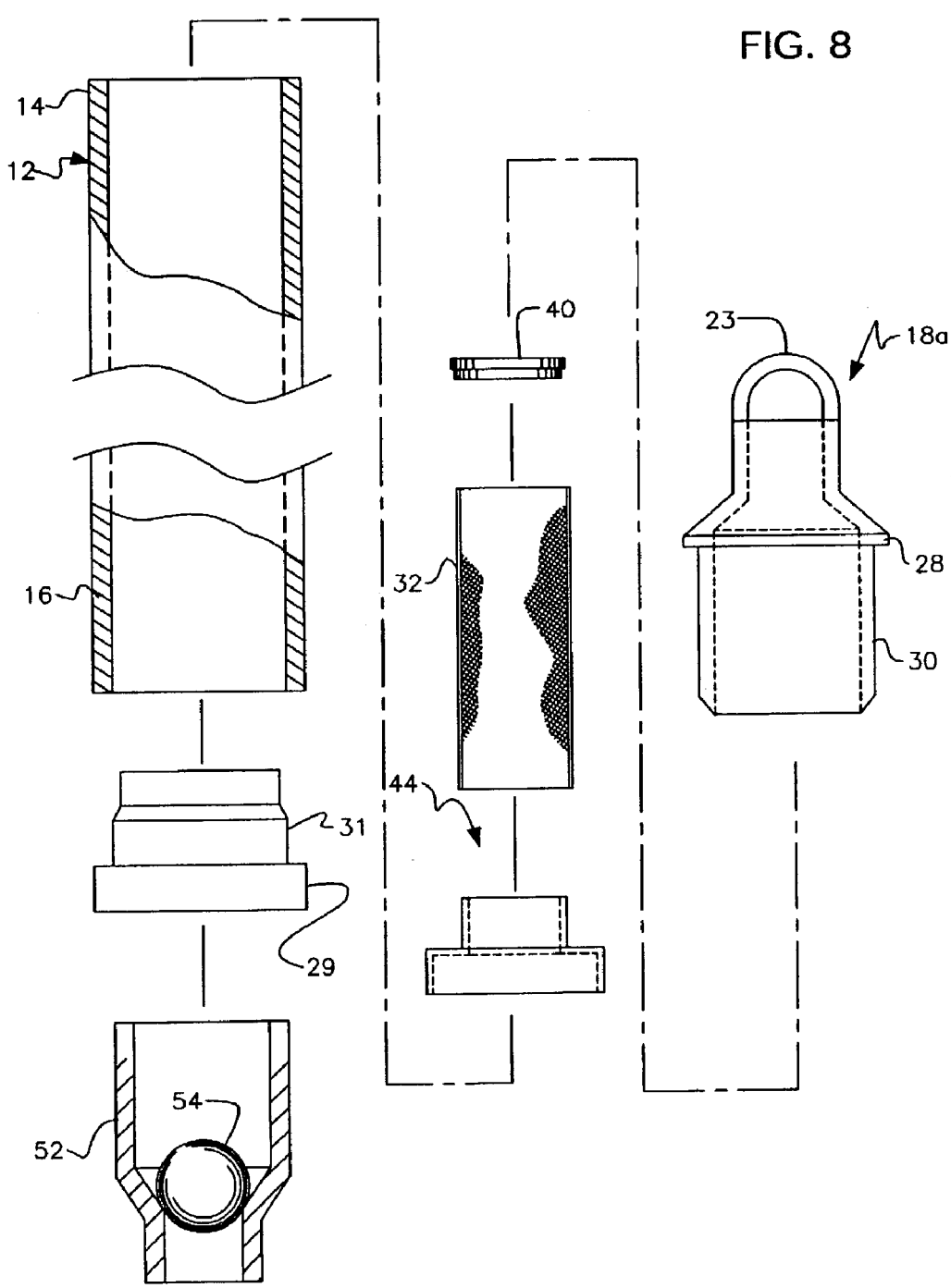
FIG. 8 is a side elevational, partially sectional assembly diagram depicting how the various parts of the second embodiment are connected to their contiguous parts.

FIG. 8 depicts how the above-described parts are assembled to form the second embodiment. Top member 18a of this embodiment is provided with conventional rope mount 23 instead of flanges 24, 26. However, a top member having flanges 24, 26 may also be used in connection with this embodiment.

In both embodiments, liquid fluid within the hollow interior of bailer 10 is constrained to flow through the cylindrical sidewalls of filter 32 when the liquid fluid is emptied from bailer 10. A need for an external filter member is thereby obviated, together with the need for a second person to hold an external filter during a bailer-emptying procedure. Accordingly, there is no need to hold bailer 10, a separate prior art filter, and the sample collection bottle all at once.

A customer having a requirement that particles of a certain size be filtered from collected samples may simply order a bailer having a filter that meets the requirement, there being no need to purchase both a filter and a bailer as separate items as was necessary prior to the disclosure of this invention. Only one individual is required to handle the sample collection and the sample filtering.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A bailer, comprising:

a main body having an elongate configuration and a hollow interior;

said main body having a trailing end and a leading end;

a top member having a first end mounted to said trailing end of said main body;

said top member having a second end in open fluid communication with an ambient environment;

a check valve housing mounted to said main body at said leading end;

a check valve means disposed within said check valve housing;

said check valve means adapted to admit liquid fluid into said hollow interior of said main body when said leading end of said bailer enters into a body of liquid fluid and said check valve means adapted to close said leading end when liquid fluid ceases flowing into said hollow interior;

a filter member disposed within said hollow interior of said main body;

said filter member having a diameter less than an inner diameter of said main body;

said filter member having a trailing end, a leading end, and a hollow interior;

an imperforate bottom fitting secured to and closing said leading end of said filter member;

said trailing end of said filter member being in fluid communication with said top member of said bailer;

a top fitting to which a trailing end of said filter member is secured;

said top fitting including a first cylindrical wall having an outer diameter substantially equal to an inner diameter of said main body;

said first cylindrical wall being snugly and slideably received within a trailing end of said main body;

said top fitting including a second cylindrical wall having an outer diameter substantially equal to said inner diameter of said filter member so that said second cylindrical wall is snugly and slideably received within said hollow interior of said filter member;

whereby liquid fluid within said hollow interior of said bailer is constrained to flow through said filter member when said liquid fluid is poured out of said open end of said top member by inverting said bailer;

whereby a need for an external filter member is obviated.

2. The bailer of claim 1, further comprising:

said main body having a cylindrical configuration;

said top member including an annular base that surmounts said trailing end of said main body;

said top member further including a depending wall of cylindrical construction mounted in depending relation from said annular base;

said depending wall having an outer diameter substantially equal to the inner diameter of said main body so that said depending wall is snugly received within said trailing end of said main body when said annular base is disposed in surmounting relation to said trailing end of said main body.

3. The bailer of claim 2, further comprising:
said top member second end having a hollow frusto-conical part and a tubular part;
said hollow frusto-conical part being a diameter-reducing part so that said tubular part has a diameter less than a diameter of said annular base;
a pair of radially-outwardly extending flanges formed on said tubular part;
an aperture formed in each radially-outwardly extending flange of said pair of radially-outwardly extending flanges;
each aperture adapted to receive a means for raising and lowering said bailer into and from a body of liquid fluid;
whereby said means for raising and lowering does not interfere with emptying an inverted bailer.

4. The bailer of claim 2, further comprising:
an annular step being formed at a juncture of said first and second cylindrical walls;
said annular step limiting the depth of penetration of said second cylindrical wall into said hollow interior of said filter member.

5. The bailer of claim 4, further comprising:
a diameter-reducing step formed in a leading end of said depending wall of said top member;
an annular space created between an inner wall of said main body and the leading end of said depending wall where said diameter-reducing space is formed;
said first cylindrical wall of said top fitting being received within said annular space when said top fitting engages said depending wall of said top member.

6. The bailer of claim 1, further comprising:
said imperforate bottom fitting including a disc-shaped base and an insert that extends into said hollow interior of said filter member, said insert being formed integrally with and positioned in concentric relationship to said disc-shaped base;
said imperforate bottom fitting including a radially-outwardly extending flange at a leading end thereof against which a leading end of said filter member abuts when said insert is fully inserted into the hollow interior of said filter member, said radially-outwardly extending flange being formed by a difference in diameter between said disc-shaped base and said insert;
whereby said top fitting and said bottom fitting cooperate with one another to hold open said hollow interior of said filter member when liquid fluid flows thereinto.

7. The bailer of claim 1, wherein said filter member is formed of polypropylene.

8. A bailer, comprising:
a main body having an elongate configuration and a hollow interior;
said main body having a trailing end and a leading end;
a top member having a first end mounted to said trailing end of said main body;
said top member having a second end in open fluid communication with an ambient environment;
a check valve housing mounted to said main body at said leading end;
a check valve means disposed within said check valve housing;
said check valve means adapted to admit liquid flow into said hollow interior of said main body when said leading end of said bailer enters into a body of liquid fluid and said check valve means adapted to close said leading end when liquid fluid ceases flowing into said hollow interior;
a filter member disposed within said hollow interior of said main body;
said filter member having a diameter less than an inner diameter of said main body;
said filter member having a trailing end, a leading end, and a hollow interior;
an imperforate top fitting secured to and closing said trailing end of said filter member;
said leading end of said filter member being in fluid communication with said check valve housing of said bailer;
a bottom fitting to which a leading end of said filter member is secured;
said bottom fitting including a first cylindrical wall having an outer diameter substantially equal to an inner diameter of said main body;
said first cylindrical wall being snugly and slideably received within a leading end of said main body;
said bottom fitting including a second cylindrical wall having an outer diameter substantially equal to said inner diameter of said filter member so that said second cylindrical wall is snugly and slideably received within said filter member; whereby liquid fluid within said hollow interior of said bailer is constrained to flow through said filter member when said liquid fluid is drained out of said bailer by opening said check valve member;
whereby a need for an external filter member is obviated.

9. The bailer of claim 8, further comprising:
said main body having a cylindrical configuration;
said top member including an annular base that surmounts said trailing end of said bailer;
said top member further including a wall of cylindrical construction mounted in depending relation from said annular base;
said depending wall having an outer diameter substantially equal to the inner diameter of said main body so that said depending wall is snugly received within said trailing end of said main body in press fit relation thereto when said annular base is disposed in surmounting relation to said trailing end.

10. The bailer of claim 8, further comprising:
said top member second end having a hollow frusto-conical part and a tubular part;
said hollow frusto-conical part being a diameter-reducing part so that said tubular part has a diameter less than a diameter of said annular base;
a pair of radially-outwardly extending flanges formed on said tubular part;
an aperture formed in each radially-outwardly extending flange of said pair of radially-outwardly extending flanges;
each aperture adapted to receive a means for raising and lowering said bailer into and from a body of liquid fluid;
whereby said means for raising and lowering does not interfere with emptying an inverted bailer.

11. The bailer of claim 8, further comprising:
an annular step being formed at a juncture of said first and second cylindrical walls;
said annular step limiting the depth of penetration of said second cylindrical wall into said hollow interior of said filter member.

12. The bailer of claim 11, further comprising:
said imperforate top fitting including a disc-shaped base and an insert formed integrally with said disc-shaped base that is concentrically positioned with respect to said disc-shaped base and that extends into said hollow interior of said filter member;

said imperforate top fitting including a radially-outwardly extending flange at a leading end thereof, said radially-outwardly extending flange being formed by a difference in diameter between said disc-shaped base and said insert;

a leading end of said filter member abutting said radially-outwardly extending flange when said insert is fully inserted into the hollow interior of said filter member;

whereby said top fitting and said bottom fitting cooperate with one another to hold open said hollow interior of said filter member when liquid fluid flows thereinto.

13. The bailer of claim 12, further comprising:

a bottom member including an annular base and an upwardly projecting wall formed integrally therewith that projects upwardly therefrom in concentric relation thereto;

said upwardly projecting wall having a diameter substantially equal to an inner diameter of said main body;

said annular base having a diameter substantially equal to an outer diameter of said main body;

an annular step formed at a juncture of said annular base and said upwardly projecting wall; and said bottom member being slideably received within the hollow interior of said main body at the leading end thereof, said annular step limiting the depth of insertion of said upwardly projecting wall into said hollow interior.

14. The bailer of claim 13, further comprising:

said bottom member annular step having a radial extent substantially equal to a thickness of said main body.

15. The bailer of claim 8, wherein said filter member is formed of polypropylene.

* * * * *